United States Patent
Backer et al.

(10) Patent No.: US 6,448,426 B1
(45) Date of Patent: Sep. 10, 2002

(54) PROCESS FOR THE PREPARATION OF SULFUR-CONTAINING ORGANOSILICON COMPOUNDS

(75) Inventors: Michael Wolfgang Backer, Vale of Glamorgan (GB); Howard Marvin Bank, Freeland, MI (US); John Michael Gohndrone, Midland, MI (US); William Charles Maki, Midland, MI (US); Charles Edmund Skinner, Midland, MI (US); Anil Kumar Tomar, Midland, MI (US); Hongjun Yue, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 09/895,721

(22) Filed: Jun. 29, 2001

(51) Int. Cl.[7] .................................................. C07F 7/08
(52) U.S. Cl. ...................................................... 556/427
(58) Field of Search ......................................... 556/427

(56) References Cited

U.S. PATENT DOCUMENTS

| | | | |
|---|---|---|---|
| 3,590,065 A | 6/1971 | Rakus et al. | 260/448.8 |
| 4,082,790 A | 4/1978 | Speier | 260/448.8 |
| 4,401,826 A | 8/1983 | Selin | 556/429 |
| 4,556,724 A | 12/1985 | Seiler et al. | 556/429 |
| 5,107,009 A | 4/1992 | Rauleder et al. | 556/429 |
| 5,399,739 A | 3/1995 | French et al. | 556/427 |
| 5,405,985 A | 4/1995 | Parker et al. | 556/427 |
| 5,466,848 A | 11/1995 | Childress | 556/427 |
| 5,468,893 A | 11/1995 | Parker et al. | 556/427 |
| 5,489,701 A | 2/1996 | Childress et al. | 556/427 |
| 5,583,245 A | 12/1996 | Parker et al. | 556/427 |
| 5,596,116 A | 1/1997 | Childress et al. | 556/427 |
| 5,663,396 A | 9/1997 | Musleve et al. | 556/427 |
| 5,840,952 A | 11/1998 | Kudo et al. | 556/429 |
| 5,859,275 A | 1/1999 | Munzenberg et al. | 556/427 |
| 5,892,085 A | 4/1999 | Munzenberg et al. | 552/427 |
| 5,936,112 A | 8/1999 | Gobel et al. | 556/427 |
| 6,066,752 A | 5/2000 | Takata et al. | 556/427 |
| 6,140,524 A | 10/2000 | Ichinohe et al. | 556/427 |
| 6,194,595 B1 * | 2/2001 | Michel et al. | 556/427 |

* cited by examiner

Primary Examiner—Paul F. Shaver
(74) Attorney, Agent, or Firm—Alan Zombeck; Jim L. De Cesare

(57) ABSTRACT

An improved process for the production of organosilicon compounds of the formula $$(RO)_{3-m}R_mSi-Alk-S_n-Alk-SiR_m(OR)_{3-m}$$

where R is independently a monovalent hydrocarbon of 1 to 12 carbon atoms,

Alk is a divalent hydrocarbon of 1 to 18 carbon atoms;

m is an integer of 0 to 2, n is a number from 1 to 8 is disclosed. The process comprises:
(A) reacting sulfur, a phase transfer catalyst, a sulfide compound having the formula $M_2S_n$ or MHS, where H is hydrogen, M is ammonium or an alkali metal, n is the same as above, and water to form an intermediate reaction product;
(B) reacting said intermediate reaction product with a silane compound of the formula;

$$(RO)_{3-m}R_mSi-Alk-X$$

where X is Cl, Br or I, and m is the same as above
(C) separating the organosilicon compound from the product mixture by adding water or a dilute acidic solution to the product mixture, and phase separating the product mixture into an organic phase containing the organosilicon compound and an aqueous phase.

12 Claims, No Drawings

PROCESS FOR THE PREPARATION OF SULFUR-CONTAINING ORGANOSILICON COMPOUNDS

FIELD OF THE INVENTION

This invention relates to a process for the production of sulfur containing organosilicon compounds by phase transfer catalysis techniques. The process involves reacting the phase transfer catalyst with the aqueous phase components of the process to create an intermediate reaction product, which is reacted with a silane compound to form a product mixture, and then the organosilicon compound is separated from the product mixture.

BACKGROUND OF THE INVENTION

Sulfur containing organosilicon compounds are useful as reactive coupling agents in a variety of commercial applications. In particular, sulfur containing organosilicon compounds have become essential components in the production of tires based on rubber vulcanates containing silica. The sulfur containing organosilicon compounds improve the physical properties of the rubber vulcanates containing silica resulting in automotive tires with improved abrasion resistance, rolling resistance, and wet skidding performance. The sulfur containing organosilicon compounds can be added directly to the rubber vulcanates containing silica, or alternately, can be used to pre-treat the silica prior to addition to the rubber vulcanate composition.

Numerous methods have been described in the art for the preparation of sulfur containing organosilicon compounds. For example, U.S. Pat. No. 5,399,739 by French et al. describes a method for making sulfur-containing organosilanes by reacting an alkali metal alcoholate with hydrogen sulfide to form an alkali metal hydrosulfide, which is subsequently reacted with an alkali metal to provide an alkali metal sulfide. The resulting alkali metal sulfide is then reacted with sulfur to provide an alkali metal polysulfide which is then finally reacted with a silane compound of the formula $X-R^2-Si(R^1)_3$, where X is either chlorine or bromine to produce the sulfur-containing organosilane.

U.S. Pat. Nos. 5,466,848, 5,596,116, and 5,489,701 describe processes for the preparation of silane polysulfides. The '848 patent process is based on first producing sodium sulfide by the reaction of hydrogen sulfide with sodium ethoxylate. The sodium sulfide is then reacted with sulfur to form the tetrasulfide, which is subsequently reacted with chloropropyltriethoxysilane to form 3,3'-bis (triethoxysilylpropyl)tetrasulfide. The '116 patent teaches a process for the preparation of polysulfides, without the use of hydrogen sulfide, by reacting a metal alkoxide in alcohol with elemental sulfur, or by reacting sodium metal with elemental sulfur and an alcohol, with a halohydrocarbylalkoxysilane such as chloropropyltriethoxysilane. The '701 patent claims a process for the preparation of silane polysulfides by contacting hydrogen sulfide gas with an active metal alkoxide solution and subsequently reacting the reaction product with a halohydrocarbylalkoxysilane such as chloropropyltriethoxysilane.

U.S. Pat. No. 5,892,085 describes a process for the preparation of high purity organosilicon disulphanes. U.S. Pat. No. 5,859,275 describes a process for the production of bis (silylorganyl) polysulphanes. Both the '085 and '275 patents describe anhydrous techniques involving the direct reaction of a haloalkoxysilane with a polysulphide.

U.S. Pat. No. 6,066,752 teaches a process for producing sulfur-containing organosilicon compounds by reacting sulfur, an alkali metal, and a halogenalkoyxsilane in the absence of a solvent or in the presence of an aprotic solvent.

Most recently, U.S. Pat. No. 6,140,524 describes a method for preparing short chain polysulfide silane mixtures of the formula $(RO)_3SiC_3H_6SiC_3H_6Si(RO)_3$ having a distribution where n falls in the range of $2.2 \leq n \leq 2.8$. The '524 method reacts metal polysulfides, typically $Na_2S_n$ with a halogenopropyltrialkoxysilane having the formula $(RO)_3SiC_3H_6X$ wherein X is a halogen, in alcohol solvent.

Alternative processes for the preparation of sulfur-containing organosilanes have been taught in the art based on the use of phase transfer catalysis techniques. Phase transfer catalysis techniques overcome many of the practical problems associated with the aforementioned prior art processes for producing sulfur-containing organosilicon compounds. Many of these problems are related to the use of solvents. In particular, the use of ethyl alcohol can be problematic because of its low flash point. Additionally, it is difficult to obtain and maintain anhydrous conditions necessary in many of the aforementioned prior art processes on an industrial scale.

Phase transfer catalysis techniques for producing sulfur-containing organosilicon compounds are taught for example in U.S. Pat. Nos. 5,405,985, 5,663,396, 5,468,893, and 5,583,245. While these patents teach new processes for the preparation of sulfur containing organosilicon compounds using phase transfer catalysis, there still exist many practical problems with the use of phase transfer techniques at an industrial scale. For example, there is a need to control the reactivity of the phase transfer catalyst in the preparation of sulfur-containing organosilanes so as to provide efficient, yet safe reactions that can be performed on an industrial scale. Furthermore, there is a need to improve the final product stability, appearance and purity. In particular, the phase transfer catalysis process of the prior art results in final product compositions containing high quantities of un-reacted sulfur species. These un-reacted sulfur species can precipitate in stored products with time causing changes in product sulfide distribution.

It is therefore an object of the present invention to provide an improved process for the production of sulfur containing organosilicon compounds based on phase transfer catalysis techniques.

It is a further object of the present invention to provide a process for producing sulfur containing organosilicon compounds based on phase transfer catalysis techniques that result in a final product composition of greater stability, purity, and appearance.

SUMMARY OF THE INVENTION

The present invention provides a process for the production of sulfur containing organosilicon compounds by phase transfer catalysis techniques. The process involves reacting a phase transfer catalyst with the aqueous phase components of the process to create an intermediate reaction product, which is then reacted a silane compound to form a product mixture. The sulfur containing organosilicon compound is then separated from the product mixture.

The improvement of the present invention is characterized by adding the phase transfer catalyst to the aqueous phase prior to mixing the aqueous phase with the silane compound for the reaction and by additional separation steps. The improvements of the present invention result in a process that is controlled and operable on an industrial scale and produces a final product composition of greater purity and appearance.

DETAILED DESCRIPTION OF THE INVENTION

The present invention is a process for the production of organosilicon compounds of the formula:

$$(RO)_{3-m}R_mSi\text{—}Alk\text{—}S_n\text{—}Alk\text{—}SiR_m(OR)_{3-m}$$

where R is independently a monovalent hydrocarbon of 1 to 12 carbon atoms; Alk is a divalent hydrocarbon of 1 to 18 carbon atoms; m is an integer of 0 to 2, n is a number from 1 to 8;
comprising:
(A) reacting sulfur, a phase transfer catalyst, a sulfide compound having the formula $M_2S_n$ or MHS, where H is hydrogen, M is ammonium or an alkali metal, and water to form an intermediate reaction product;
(B) reacting said intermediate reaction product with a silane compound of the formula;

$$(RO)_{3-m}R_mSi\text{—}Alk\text{—}X \text{ where X is Cl, Br or I.}$$

to form a product mixture
(C) separating the organosilicon compound from the product mixture.

Examples of sulfur containing organosilicon compounds which may be prepared in accordance with the present invention are described in U.S. Pat. Nos. 5,405,985, 5,663, 396, 5,468,893, and 5,583,245, which are hereby incorporated by reference. The preferred sulfur containing organosilicon compounds which are prepared in accordance with the present invention are the 3,3'-bis(trialkoxysilylpropyl) polysulfides. The most preferred compounds are 3,3'-bis (triethoxysilylpropyl)disulfide and 3,3'-bis (triethoxysilylpropyl)tetrasulfide.

The first step of the process of the present invention involves reacting sulfur, a phase transfer catalyst, a sulfide compound having the formula $M_2S_n$ or MHS, where H is hydrogen, M is ammonium or an alkali metal, n is the same as above, and water to form an intermediate reaction product. The sulfur used in the reaction of the present invention is elemental sulfur. The type and form are not critical and can include those commonly known and used. An example of a suitable sulfur product is 100 mesh refined sulfur powder from Aldrich, Milwaukee Wis.

Sulfide compounds of the formula $M_2S_n$ or MHS are also added to the aqueous phase in the first step of the present invention. M represents an alkali metal or ammonium group and H represents hydrogen. Representative alkali metals include potassium, sodium, rubidium, or cesium. Preferably M is sodium. Generally, MHS compounds are used preferentially when the average value of n in the resulting product formula, $(RO)_{3-m}R_mSi\text{—}Alk\text{—}S_n\text{—}Alk\text{—}SiR_m(OR)_{3-m}$ is desired to be 2. Suitable examples of the MHS compound include, but are not limited to NaHS, KHS, and NH$_4$HS. When the sulfide compound is an MHS compound, NaHS is preferred. Suitable examples of the NaHS compound include, but are not limited to NaHS flakes (containing 71.5–74.5% NaHS) and NaHS liquors (containing 45–60% NaHS) from PPG of Pittsburgh, Pa. $M_2S_n$ compounds are used preferentially when the average value of n in the resulting product formula, $(RO)_{3-m}R_mSi\text{—}Alk\text{—}S_n\text{—}Alk\text{—}SiR_m(OR)_{3-m}$ is desired to be 4. Suitable examples of compounds of $M_2S_n$ include, but are not limited to; Na$_2$S, K$_2$S, Cs$_2$S, (H$_4$)$_2$S, Na$_2$S$_2$, Na$_2$S$_3$, Na$_2$S$_4$, Na$_2$S$_6$, K$_2$S$_2$ K$_2$S$_3$, K$_2$S$_4$, K$_2$S$_6$, and (NH$_4$)$_2$S$_2$. Preferably the sulfide compound is Na$_2$S. A particular preferred sulfide compound is sodium sulfide flakes (containing 60–63% Na$_2$S) from PPG of Pittsburgh, Pa.

The amount of sulfur and sulfide compound used in the process of the present invention can vary, but preferably the molar ratio of $S/M_2S_n$ or S/MHS ranges from 0.3 to 5. The molar ratio of sulfur/sulfide compound can be used to affect the final product distribution, that is the average value of n in the formula, $(RO)_{3-m}R_mSi\text{—}Alk\text{—}S_n\text{—}Alk\text{—}SiR_m(OR)_{3-m}$. When the average value of n is desired to be 4 in the product formula, $(RO)_{3-m}R_mSi\text{—}Alk\text{—}S_n\text{—}Alk\text{—}SiR_m(OR)_{3-m}$, the preferred range for the ratio of sulfur/sulfide compound is from 2.7 to 3.2. When the average value of n is desired to be 2 in the product formula, $(RO)_{3-m}R_mSi\text{—}Alk\text{—}S_n\text{—}Alk\text{—}SiR_m(OR)_{3-m}$, the preferred range for the ratio of sulfur/sulfide compound is from 0.3 to 0.6.

The phase transfer catalysts operable in the present invention are the quaternary onium cations. Examples of the quaternary onium cations that can be used as phase transfer catalysts in the present invention are described in U.S. Pat. No. 5,405,985, which is hereby incorporated by reference. Preferably, the quaternary onium cation is tetrabutyl ammonium bromide or tetrabutyl ammonium chloride. The most preferred quaternary onium salt is tetrabutyl ammonium bromide. A particularly preferred quaternary onium salt is tetrabutyl ammonium bromide (99%) from Aldrich Chemical of Milwaukee, Wis.

The amount of the phase transfer catalyst used in the process can vary. Preferably the amount of phase transfer catalyst is from 0.1 to 10 weight %, and most preferably from 0.5 to 2 weight % based on the amount of silane compound used.

The phase transfer catalyst, sulfur, and sulfide compounds are mixed in water and allowed to react to form an intermediate reaction product. The amount of water used to create the intermediate reaction product can vary, but is preferably based on the amount of the silane compound used in the process. Water can be added directly, or indirectly, as some water may already be present in small amounts in other starting materials. For purposes of the present invention, it is preferable to calculate the total amount of water present, that is, accounting for all water added either directly or indirectly. Preferably, the total amount of water used to create the intermediate reaction product is 1 to 100 weight % of the silane compound used, with a range of 2.5 to 70 weight % being more preferred. Most preferred is a range of 20 to 40 weight % of water used for the intermediate reaction product based on the amount of silane compound used.

The reaction of the first step involves mixing sulfur, a sulfide compound, a phase transfer catalyst, and water together in a reaction vessel. The reaction of the first step can be conducted at a variety of temperatures, but generally in the range of 40–100° C. Preferably, the reaction is conducted at a temperature ranging from 65–95° C. Generally, the first step can be conducted at various pressures, but preferably the first step reaction is conducted at atmospheric pressure. The time needed for the reaction of the first step to occur is not critical, but generally ranges from 5 to 30 minutes.

The second step of the process of the present invention involves reacting the intermediate reaction product with a silane compound of the formula;

$$(RO)_{3-m}R_mSi\text{—}Alk\text{—}X$$

Each R is an independently selected hydrocarbon group containing 1 to 12 carbon atoms. Thus, examples of R include methyl, ethyl, propyl, butyl, isobutyl, cyclohexyl, or phenyl. Preferably, R is a methyl or ethyl group. In the formula $(RO)_{3-m}R_mSi$—Alk—X, m is an integer and can have a value from 0 to 2. Preferably, m is equal to 0. Alk is a divalent hydrocarbon group containing 1 to 18 carbon atoms. Alk can be for example; ethylene, propylene, butylene, or isobutylene. Preferably Alk is a divalent hydrocarbon group containing 2 to 4 carbon atoms, and most preferably, Alk is a propylene group. X is a halogen atom selected from chlorine, bromine, or iodine. Preferably X is chlorine. Examples of silane compounds that may be used in the present invention include chloropropyl triethoxy silane, chloropropyl trimethoxy silane, chloroethyl triethoxy silane, chlorobutyl triethoxy silane, chloroisobutylmethyl diethoxy silane, chloroisobutylmethyl dimethoxy silane, chloropropyldimethyl ethoxy silane. Preferably, the silane compound of the present invention is chloropropyl triethoxy silane (CPTES).

The silane compound, $(RO)_{3-m}R_mSi$—Alk—X, can be reacted directly with the intermediate reaction product described above, or alternatively, the silane compound can be dispersed in an organic solvent. Representative examples of organic solvents include toluene, xylene, benzene, heptane, octane, decane, chlorobenzene and the like. When an organic solvent is used, the preferred organic solvent is toluene.

When conducting the process of the present invention, preferably the silane compound is reacted directly with the intermediate reaction product described above.

The amount of the silane compound $(RO)_{3-m}R_mSi$—Alk—X used in the process of the present invention can vary. An example of a suitable molar range includes from 1/10 to 10/1 based on the amount of sulfide compound used. When the average value of n is desired to be 4 in the product formula, $(RO)_{3-m}R_mSi$—Alk—$S_n$—Alk—$SiR_m(OR)_{3-m}$, the silane compound $(RO)_{3-m}R_mSi$—Alk—X is generally used from 2.0 to 2.10 in molar excess of the $M_2S_n$ sulfide compound, with a range of 2.01 to 2.06 being the most preferable. When the average value of n is desired to be 2 in the product formula, $(RO)_{3-m}R_mSi$—Alk—$S_n$—Alk—$SiR_m(OR)_{3-m}$, the silane compound $(RO)_{3-m}R_mSi$—Alk—X is preferably used from 1.8 to 2.1 in molar excess of the MHS sulfide compound, with a range of 1.9 to 2.0 being the most preferable.

When conducting the second step of the present invention, preferably the silane compound is added to the intermediate reaction product at such a rate so as to maintain a constant reaction temperature. The reaction of the second step of the present invention can be conducted at a variety of temperatures, but generally is conducted in the range of 40–100° C. Preferably, the reaction is conducted at a temperature ranging from 65–95° C. Generally, the second step can be conducted at a various pressures, but preferably the second step reaction is conducted at atmospheric pressure. The time needed for the reaction of the second step to occur is not critical, but generally ranges from 5 minutes to 6 hours.

The process of the present invention produces organosilicon compounds that are dialkyl polysulfides, containing on average 2–6 sulfur atoms, via a phase transfer catalyzed reaction of an aqueous phase containing a polysulfide and a silane compound. A typical reaction of the present invention is exemplified according to the following equation;

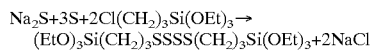

$Na_2S+3S+2Cl(CH_2)_3Si(OEt)_3 \rightarrow$
$(EtO)_3Si(CH_2)_3SSSS(CH_2)_3Si(OEt)_3+2NaCl$ In a typical run, stoichiometric amounts of sulfur, $Na_2S$ are added to water, heated to 65° C. and mixed until all solids are dispersed. An aqueous solution of the phase transfer catalyst is added. The organosilane compound is then added to the aqueous solution at such a rate to control the exothermic reaction, and maintain a temperature in the range of 40 to 110° C. Preferably the reaction temperature is maintained at 60 to 95° C. The reaction progress can be monitored by the consumption of the organosilane starting material. The precipitation of a salt, for example sodium chloride if $Na_2S$ is used as a starting reactant, also indicates progression of the reaction. The amount of catalyst and reaction temperature affects the reaction time necessary for completion.

At the end of the reaction, a product mixture is produced containing an organic phase, an aqueous phase, and possibly precipitated solid materials that can include salts formed during the reaction. The organic phase contains the organosilane compound. The present invention provides for processing steps to enhance the separation of the organosilane compound from the product mixture. Furthermore, the present invention provides additional processing steps that provide for an organosilane compound having enhanced purity.

Step (C) of the present invention involves separating the organosilicon compound $(RO)_{3-m}R_mSi$—Alk—$S_n$—Alk—$SiR_m(OR)_{3-m}$ from the product mixture. This separation can be the phase separation of the organic and aqueous phase, resulting directly from the reaction from steps (A) and (B) above. Alternatively, if precipitated salts are formed during the reaction, the salts can be separated first by a filtering process or decanting method prior to the phase separation. Preferably, water or a dilute acidic solution is added to the product mixture prior to separation. The addition of water or a dilute acidic solution can enhance the phase separation by dissolving some or all of the precipitated salts. The amount of water or dilute acidic solution that is added during this step can vary from 10 to 50% based on the weight of the amount of silane compound used, preferably, the amount of water or dilute acidic solution added is from 20 to 40 wt % based on the amount of the silane compound used, and most preferably from 25 to 35. When a dilute acidic solution is used, it can be any of the common acids, for example HCl, $HNO_3$, $H_2SO_4$, or the like, having a normal (N) concentration of 0.0000001 to 5, preferably 0.01 to 1. The dilute acidic solution can also be prepared by the addition of a chlorosilane to water. Examples of chlorosilanes that can be used to create the dilute acidic solution include trichlorosilane, trichloromethylsilane, dimethyldichlorosilane, dimethylchlorosilane, trimethylchlorosilane. When a chlorosilane is used to create the dilute acidic solution, preferably 0.5 to 10 wt % chlorosilane can be used to prepare the dilute acidic solution, with 1 to 5 wt % being the most preferred. When a chlorosilane is used to create the dilute acidic solution, the chlorosilane is preferably trimethylchlorosilane.

Following the addition of water or a dilute acidic solution to the product mixture, the organosilicon compound is isolated from the product mixture by phase separating the organic phase and aqueous phase. The organic phase containing the organosilicon compound can be further subjected to a drying step. One example of the drying step can be to treat the organic phase under vacuum to remove any volatile organic materials present along with any residual water that may be present. This drying step can involve, for example, heating the organic phase to a temperature of 20 to 160° C. under a reduced pressure of 5 to 35 mm Hg (0.67 to 4.65 kPa), preferably the conditions are 90 to 120° C. at 5 to 25 mm Hg (0.67 to 3.33 kPa). Alternatively, the drying step of the organic phase can involve the use of a thin film stripper to remove volatile organics materials and residual water content in the organic phase. Yet another technique for the drying step of the organic phase can be to contact the organic phase containing the organosilicon compound with a desiccant material. The desiccant material can be any solid material known in the art to remove trace quantities of water in organic phases. These include known ionic hygroscopic materials like sodium sulfate, magnesium sulfate, and the like, or silicate based materials such as zeolites, silica, aluminasilicates, and the like. The preferred desiccant material is either sodium sulfate or magnesium sulfate, with sodium sulfate being the most preferred.

The dried organic phase can be subjected to additional steps according to the present invention that result in further improvements of the organosilicon compound final purity and appearance. The organic phase containing the organosilicon compound can be cooled to a temperature below 15° C. This cooling step results in the precipitation of un-reacted sulfur and sulfur compounds. Preferably, the organic phase containing the organosilicon compound is cooled to a temperature in the range of −20 to 30° C., and most preferably to a temperature in the range of −20 and −10° C. The precipitated un-reacted sulfur and sulfur compounds can then be separated, for example by filtration, from the organic phase containing the organosilicon compound. The present inventors have found that removing un-reacted sulfur and sulfur compounds minimizes or eliminates further precipitation of sulfur and un-reacted sulfur compounds with time. As a result, the long-term storage stability of the organosilicon compound is enhanced by producing a composition that does not change with time, or results in a product composition containing solid precipitates.

The following examples are provided to illustrate the present invention. These examples are not intended to limit the scope of the claims herein.

EXAMPLES

Example 1

The following general procedure was used to conduct runs 1–6, shown in Table I.

A 100 ml 3 necked round bottom flask, fitted with a condenser, nitrogen sweep, and magnetic stirrer, was charged with varying amounts of $Na_2S$, sulfur, (as shown in Table I) and 6.25 g of water. The contents were heated to 70° C. while stirring under nitrogen. After the $Na_2S$ and sulfur dissolved, varying amounts of the catalyst (Table I) tetrabutylammonium bromide obtained from Aldrich of Milwaukee, Wis., were added and allowed to mix for 10 minutes. Then, a solution containing 25 g of chloropropyltriethoxysilane (CPTES) and 1.25 g of toluene (used for a reference standard for gas chromatographic analysis) was added dropwise at such a rate to maintain the reaction temperature in the range of 70–80° C. The reaction was monitored by gas chromatographic methods and allowed to proceed until all the CPTES had been consumed or until no further change in its concentration was observed. After completion of the reaction, the reaction mixture was allowed to cool to 25° C. and then 14.2 g of water were added to the reaction mixture to dissolve precipitated sodium chloride. The reaction mixture was then phase separated. The resulting organic phase was then treated with sodium sulfate and filtered. The resulting filtrate was then cooled and stored at a temperature of −13° C., and subsequently filtered again.

The distribution of the various sulfur containing organosilicon compounds were analyzed by high-pressure liquid chromatography (HPLC). Typical run conditions for HPLC analysis were as follows: 8–9 drops of the reaction sample were diluted in 8.5 g of cyclohexane, which was then filtered through a 0.2 $\mu$m PTFE membrane (e.g. PURADISC™ 25TF of Whatman®) into a vial, a 10 $\mu$l sample of the filtrate was injected via an autosampler into a HPLC system (e.g. Hewlett-Packard 1050). The sample was fractionated on a Lichrosorp RP18 column (e.g. Alltech Assoc., Inc; 250 mm×4.6 mm, 10 $\mu$m) using a mixture of 96% acetonitrile and 4% tetrahydrofurane (vol/vol) as mobile phase. The fractions were investigated via UV-absorption detector using 254 nm as the appropriate excitation wavelength. Different UV-sensitivities of every single sulfide species were averaged by division of the respective peak area through specific, empirically evaluated, response factors* (RF) listed below that reflect the hyperchromy with every sulfur atom in the chain and elemental sulfur.

| HPLC Response Factors. | | | | | | | | | |
|---|---|---|---|---|---|---|---|---|---|
| S2 | S3 | S4 | S5 | S6 | S7 | S8 | S9 | S10 | $S_{elem.}$ |
| 1.0 | 3.52 | 6.39 | 9.78 | 13.04 | 17.39 | 20.87 | 26.08 | 31.30 | 37.26 |

*As reported by H. D. Luginsland, "Reactivity of the Sulfur Functions of the Disulfane Silane TESPD and the Tetrasulfane Silane TESPT"; Rubber Division, American Chemical Society; Chicago, IL, April 13–16, 1999.

The products were consistent with the general formula $(EtO)_3Si$—$CH_2CH_2CH_2$—$S_n$—$CH_2CH_2CH_2$—$Si(OEt)_3$. The percentage of each discrete organosilicon sulfur species in the composition, as represented by the value of $S_n$ in the above formula, is shown in Table II.

The results from Runs 1–6 show the effects of using various stoichiometric ratios of CPTES and sodium sulfides based on sodium and sulfide, effect of catalyst concentration, reaction temperature, and mole ratio of $S/S^{-2}$.

TABLE I

| Run # | $Na_2S$ [g] | ratio CPTES/ $Na^+$ or $S^{2-}$ moles | Sulfur [g] | Temp. [° C.] | Cat. Conc.[a] [wt %] | Run Time[b] [min] | Phase Sep. | Product color |
|---|---|---|---|---|---|---|---|---|
| 1 | 6.74[c] | Na: 1.000<br>$S^{2-}$: 1.886 | 5.80 | 70 | 1.25 | 150[c] | bad[f,g] | orange-brown |
| 2 | 6.36[c] | Na: 1.060<br>$S^{2-}$: 2.000 | 4.99 | 70 | 2.50 | 135 | good | yellow |
| 3 | 6.36[c] | Na: 1.060<br>$S^{2-}$: 2.000 | 4.99 | 65 | 2.50 | 170 | good | yellow |
| 4 | 6.74[c] | Na: 1.000<br>$S^{2-}$: 1.886 | 4.99 | 65 | 2.50 | 115 | bad[f,g] | red |

TABLE I-continued

| Run # | Na$_2$S [g] | ratio CPTES/ Na$^+$ or S$^{2-}$ moles | Sulfur [g] | Temp. [° C.] | Cat. Conc.[a] [wt %] | Run Time[b] [min] | Phase Sep. | Product color |
|---|---|---|---|---|---|---|---|---|
| 5 | 6.55[c] | Na: 1.029 S$^{2-}$: 1.941 | 4.99 | 65 | 2.50 | 230 | good | yellow |
| 6 | 6.75[d] | Na: 1.001 S$^{2-}$: 1.997 | 4.99 | 65 | 2.50 | 215 | bad[f,g] | red |

[a] based on amount of CPTES;
[b] approximate run time from start of CPTES addition until cooling cycle;
[c] Na$_2$S flakes containing 56.20 wt % Na$_2$S and 5.20 wt % NaSH;
[d] Na$_2$S flakes containing 59.75 wt % Na$_2$S and 0.26 wt % NaSH;
[e] reaction was stopped incompletely because of high peak value of ethanol in gas chromatogram;
[f] washed with brine;
[g] washed with 1.0-normal HCl solution.

TABLE II

Sulfide distribution and Sulfur Rank by HPLC

| Run # | S$_2$ [%] | S$_3$ [%] | S$_4$ [%] | S$_5$ [%] | S$_6$ [%] | S$_7$ [%] | S$_8$ [%] | S$_9$ [%] | S$_{10}$ [%] | S$_{elem.}$ [%] | S$_n$ |
|---|---|---|---|---|---|---|---|---|---|---|---|
| Run #1 crude | 13.05 | 27.98 | 25.46 | 16.96 | 8.63 | 3.96 | 1.91 | 0.86 | 0.32 | 0.87 | 4.00 |
| Run #1 washed with 1N HCl in brine | 15.29 | 27.03 | 25.89 | 16.64 | 8.27 | 3.62 | 1.63 | 0.69 | 0.23 | 0.72 | 3.91 |
| Run #2 | 17.52 | 27.69 | 24.71 | 15.88 | 7.58 | 3.42 | 1.56 | 0.69 | 0.26 | 0.68 | 3.83 |
| Run #3 filtered | 16.54 | 27.72 | 25.20 | 15.86 | 7.86 | 3.55 | 1.62 | 0.70 | 0.22 | 0.72 | 3.86 |
| Run #3 stored at -13° C. | 17.55 | 30.61 | 27.39 | 14.54 | 6.05 | 2.30 | 0.94 | 0.41 | — | 0.21 | 3.65 |
| Run #3 crude | 18.01 | 27.72 | 25.30 | 15.31 | 7.49 | 3.33 | 1.51 | 0.59 | — | 0.74 | 3.80 |
| Run #4 filtered crude | 14.67 | 30.51 | 25.10 | 16.01 | 7.78 | 3.35 | 1.43 | 0.50 | 0.21 | 0.46 | 3.83 |
| Run #4 washed with 1N HCl in brine | 15.86 | 28.91 | 24.54 | 16.07 | 8.12 | 3.68 | 1.61 | 0.65 | 0.46 | 0.19 | 3.85 |
| Run #5 | 14.22 | 31.18 | 25.47 | 15.91 | 7.54 | 3.25 | 1.37 | 0.46 | 0.19 | 0.42 | 3.82 |
| Run #6 | 15.16 | 29.31 | 25.00 | 16.23 | 7.98 | 3.57 | 1.57 | 3.86 | 0.57 | 0.61 | 3.86 |

TABLE III

Precipitation and color observations for Runs 1–7

| Run | Observation: |
|---|---|
| 1 | decanted organic phase was dark yellow, contained a high amount of dark yellow powder and needles<br>HCl washed and decanted portion was bright yellow with few clear crystals |
| 2 | unfiltered organic phase was bright yellow, contained needles and rhombs within powder<br>filtered (through 5 μm Acrodisc ® filter) sample was bright yellow, contained only small amounts of nearly colorless crystals |
| 3 | filtered sample was bright yellow, contained only small amount of nearly colorless crystal<br>sample stored overnight at −15' C. and filtered again was bright yellow, showed no further precipitation |
| 4 | decanted organic phase was bright yellow, contained only small amounts of powder<br>sample dried over Na$_2$SO$_4$ and filtered was clear and bright yellow, no visible precipitation<br>acid-washed sample was bright yellow, contained large amount of powder |
| 5 | filtered sample which was stored overnight at −15' C. was bright yellow, contained small amounts of white powder, when filtered again and stored at ambient temperature, no further precipitation was visible |
| 6 | acid washed sample, dried over Na$_2$SO$_4$ and filtered, was dark yellow, no powder or crystals, but contained small black to green particles) |

Example 2

The following general procedure was used to conduct runs 7–15, as summarized in Table III. A 1 liter or 1.5 liter 3 necked reactor, fitted with a condenser, internal thermometer, one baffle, nitrogen sweep, and stirrer, was charged with varying amounts of Na$_2$S, sulfur, (as shown in Table III) and 112.5 g of water. Contents were mixed at a constant stirring speed of 300 rpm and heated to 70° C. under nitrogen. After the Na$_2$S and sulfur dissolved, varying amounts of the catalyst, tetrabutylammonium bromide obtained from Aldrich of Milwaukee, Wis., were added and allowed to mix for 10 minutes. Then, CPTES (amount as shown in Table III) was added dropwise at such a rate to maintain the reaction temperature. The reaction was monitored by gas chromatographic methods and allowed to proceed until all the CPTES had been consumed or until no further change in its concentration was observed. After completion of the reaction, the reaction mixture was allowed to cool to 25° C. and then 137.5 g of water was added to the reaction mixture to dissolve precipitated sodium chloride. The reaction mixture was then phase separated. The resulting organic phase was filtered then treated with sodium sulfate and re-filtered. The resulting filtrate was then cooled and stored at a temperature of −13° C., and subsequently filtered again.

The final organic product from these runs was analyzed for the various polysulfide organosilicon compounds by HPLC. The products were consistent with the general formula (EtO)$_3$Si—CH$_2$CH$_2$CH$_2$—S$_n$—CH$_2$CH$_2$CH$_2$—Si (OEt)$_3$. The percentage of each discrete organosilicon sulfur species in the composition, as represented by the value of S$_n$, is shown in Table IV.

TABLE IV

Conditions for Runs 7–15

| run | Reactor Volume [l] | baffle | Run Time[a] [h] | Temp. [°C.] | CPTES [g] | CPTES to $Na_2S$ | Sulfur to $Na_2S$ | Cat. [wt %] | Prod. Color |
|---|---|---|---|---|---|---|---|---|---|
| 7 | 1.0 | 4 | 5 | 65 | 300 | 2 | 3.0 | 0.8 | red |
| 8 | 1.5 | 1 | >12 | 65 | 450 | 2 | 3.0 | 0.2 | red |
| 9 | 1.5 | 1 | 5.5 | 65 | 450 | 2 | 3.0 | 0.8 | red |
| 10 | 1.5 | 1 | 5.5 | 65 | 454.5 | 2.02 | 3.0 | 0.8 | orange |
| 11 | 1.5 | 1 | 5.5 | 65 | 463.5 | 2.06 | 3.0 | 0.8 | green |
| 12 | 1.5 | 1 | 5.5 | 65 | 463.5 | 2.06 | 2.8 | 0.8 | green |
| 13 | 1.0 | 4 | 4 | 80 | 463.5 | 2.06 | 3.0 | 0.8 | yellow |
| 14 | 1.5 | 1 | 4.5 | 80 | 463.5 | 2.06 | 3.0 | 0.8 | light green |
| 15 | 1.0 | 1 | 2.5 | 80 | 463.5 | 2.06 | 3.0 | 1.6 | dark yellow |

[a] approximate run time from start of CPTES addition until cooling cycle.

TABLE V

Sulfide distribution and Sulfur Rank by HPLC

| run # | $S_2$ [%] | $S_3$ [%] | $S_4$ [%] | $S_5$ [%] | $S_6$ [%] | $S_7$ [%] | $S_8$ [%] | $S_9$ [%] | $S_{10}$ [%] | $S_{elem.}$ [%] | $S_n$ |
|---|---|---|---|---|---|---|---|---|---|---|---|
| 7 | 14.11 | 30.99 | 25.03 | 16.04 | 7.65 | 3.41 | 1.56 | 0.58 | 0.23 | 0.40 | 3.84 |
| 8 | 15.51 | 31.11 | 24.57 | 15.72 | 7.35 | 3.32 | 1.46 | 0.56 | — | 0.41 | 3.79 |
| 9 | 16.10 | 32.20 | 24.50 | 15.02 | 6.94 | 2.97 | 1.28 | 0.50 | 0.18 | 0.30 | 3.73 |
| 10 | 16.10 | 29.81 | 24.67 | 15.76 | 7.60 | 3.34 | 1.49 | 0.58 | 0.21 | 0.43 | 3.81 |
| 11 | 17.27 | 28.96 | 24.29 | 15.63 | 7.59 | 3.40 | 1.54 | 0.59 | 0.24 | 0.49 | 3.80 |
| 12 | 19.10 | 31.30 | 24.25 | 14.49 | 6.40 | 2.68 | 1.14 | 0.39 | — | 0.24 | 3.63 |
| 13 | 15.56 | 30.22 | 24.98 | 15.91 | 7.57 | 3.25 | 1.38 | 0.52 | 0.19 | 0.43 | 3.81 |
| 14 | 17.94 | 28.49 | 24.84 | 15.55 | 7.24 | 3.22 | 1.40 | 0.56 | 0.22 | 0.55 | 3.78 |
| 15 | 21.00 | 28.53 | 23.92 | 14.49 | 6.95 | 2.87 | 1.20 | 0.43 | — | 0.61 | 3.67 |

TABLE VI

Precipitation and color observations for Runs 7–15

| Run | Observation: |
|---|---|
| 7 | dark yellow to orange, stored at −15° C., sample contained a large amount of yellow powder and a greenish "gel" (can be residual water) stored at room temperature, completely filled bottle light red, half filled bottle bright yellow, both of the samples contained black particles, but no further precipitation occurred. |
| 8 | organic phase was clear and bright yellow, aqueous phase was clear orange, phases were separated by a black and green solid |
| 9 | greenish yellow sample without precipitation, contained only a few black particles, not stored at −15° C. |
| 10 | stored at room temperature, sample was dark yellow with black ring on glass wall, stored in freezer; stored at −15° C., sample was orange red, large amount of brown precipitate was formed, black ring on top was formed |
| 11 | stored at room temperature, sample was yellow with black particles on bottom stored at −15° C., sample was green, large amount of yellow precipitate was formed |
| 12 | samples were green with black particles on the bottom, no precipitate formed at −15° C. |
| 13 | samples were brown green with black particles on the bottom, no precipitate was formed at −15° C. |
| 14 | green, no particles visible, only a few needles formed at −15° C. |
| 15 | green, no particles visible at room temperature, large amount of needles formed at −15° C. |

We claim:

1. A process for the production of organosilicon compounds of the formula:

$$(RO)_{3-m}R_mSi-Alk-S_n-Alk-SiR_m(OR)_{3-m}$$

where R is independently a monovalent hydrocarbon of 1 to 12 carbon atoms; Alk is a divalent hydrocarbon of 1 to 18 carbon atoms; m is an integer of 0 to 2, n is a number from 1 to 8;

comprising:

(A) reacting sulfur, a phase transfer catalyst, a sulfide compound having the formula $M_2S_n$ or MHS, where H is hydrogen, M is ammonium or an alkali metal, and water to form an intermediate reaction product;

(B) reacting said intermediate reaction product with a silane compound of the formula;

$$(RO)_{3-m}R_mSi-Alk-X$$

where X is Cl, Br or I to form a product mixture (C) separating the organosilicon compound from the product mixture.

2. The process of claim 1 where the organosilicon compound is separated from the product mixture by (D) adding water or a dilute acidic solution to the product mixture, and (E) phase separating the product mixture into an organic phase containing the organosilicon compound and an aqueous phase.

3. The process of claim 2 wherein the weight percentage of water or dilute acidic solution to the silane compound is 10–50%.

4. The process of claim 2 wherein the weight percentage of water or dilute acidic solution to the silane compound is 20–40%.

5. The process of claim 2 wherein the organic phase containing the organosilicon compound is dried.

6. The process of claim 5 wherein the organic phase containing the organosilicon compound is dried by heating the organic phase at reduced pressures.

7. The process of claim 5 wherein the organic phase containing the organosilicon compound is dried by contacting the organic phase with a solid desiccant.

8. The process of claim 7 wherein the solid desiccant is sodium sulfate or magnesium sulfate.

9. The process of claim 8 where the desiccant is sodium sulfate.

10. The process of claim 2 further comprising the steps;
   (F) cooling the organic phase containing the organosilicon compound below 15° C. to precipitate un-reacted sulfur compounds,
   (G) separating the organic phase containing the organosilicon compound from the precipitated un-reacted sulfur compounds.

11. The process of claim 10 where the organic phase containing the organosilicon compound is cooled to a temperature in the range of –20 to 10° C.

12. The process of claim 11 where the organic phase containing the organosilicon compound is cooled to a temperature in the range of –15 to –10° C.

* * * * *